US007354723B2

(12) United States Patent
Christgau et al.

(10) Patent No.: US 7,354,723 B2
(45) Date of Patent: Apr. 8, 2008

(54) ASSAY OF ISOMERISED AND/OR OPTICALLY INVERTED PROTEINS AND PROTEIN FRAGMENTS

(75) Inventors: Stephan Christgau, Gentofte (DK); Dennis B. Henriksen, Allerød (DK); Paul A. C. Cloos, København (DK)

(73) Assignee: Nordic Bioscience Dagnostics A/S, Herlev (DK)

(*) Notice: Subject to any disclaimer, the term of this patent is extended or adjusted under 35 U.S.C. 154(b) by 0 days.

(21) Appl. No.: 10/154,424

(22) Filed: May 23, 2002

(65) Prior Publication Data

US 2005/0054014 A1 Mar. 10, 2005

Related U.S. Application Data

(63) Continuation of application No. PCT/EP00/11720, filed on Nov. 24, 2000.

(60) Provisional application No. 60/343,384, filed on Dec. 21, 2001.

(30) Foreign Application Priority Data

Nov. 26, 1999 (GB) ................................. 9928052.1

(51) Int. Cl.
G01N 33/53 (2006.01)
C07K 5/023 (2006.01)
C07K 5/027 (2006.01)
(52) U.S. Cl. .................... 435/7.1; 530/332; 530/840
(58) Field of Classification Search ...................... None
See application file for complete search history.

(56) References Cited

U.S. PATENT DOCUMENTS

2003/0216319 A1* 11/2003 Cloos et al. .................. 514/13

FOREIGN PATENT DOCUMENTS

| WO | WO 96/30765 | | 10/1996 |
| WO | WO 98/08098 | * | 2/1998 |
| WO | WO 98/26286 | | 6/1998 |
| WO | WO 01/13110 A2 | * | 2/2001 |

OTHER PUBLICATIONS

Harlow and Lane, "Antibodies: A Laboratory Manual," Cold Spring Harbor Laboratory, 1988, Chapter 5, p. 76.*
Burgess et al. J Cell Bio. 111:2129-2138, 1990.*
Lazar et al. Molecular and Cellular Biology 8:1247-1252 (1988).*
Tao et al., The Journal of Immunology, 143:2595-2601 (1989).*
Biology-Online.org Online Dictionary, definition of "isomer.", 2005.*
Garnero et al. "Cross sectional evaluation of biochemical markers of bone, cartilage, and synovial tissue metabolism in patients with knee osteoarthritis: relations with disease activity and joint damage" (2001) Ann Rheum Dis 60:619-626.*

Garnero et al. "Biochemical markers of joint tissue turnover in early rheumatoid arthritis" (2003) Clin Exp Rheumatol 21(5 Suppl 31):S54-S58.*
A Laboratory Manual, E. Harlow and D. Lane, ed., Cold Spring Harbor Laboratory (Cold Spring Harbor, NY, 1988), p. 76.*
Janeway et al., Immunobiology: The Immune System in Health and Disease, Fourth Edition, 1999: Elsevier Science Ltd/Garland Publishing, London, UK, pp. 34-35, 46-47, and 599.*
D'Amico et al. "Pathophysiology of proteinuria" Kidney International, vol. 63 (2003), pp. 809-825.*
Skoumal et al. (2004) Arthritis Res Ther 6:73-74.*
Roughley, P.J. and El-Maadaway, S., "The Use of Biochemical Markers of Bone and Cartilage Metabolism to Monitor Osteoarthritis-Dreams and Reality" The Journal of Rheumatology 30:5, p. 910-912, 2003.*
Poole, R. "Can Serum Biomarker Assays Measure the Progression of Cartilage Degeneration in Osteoarthritis?" Arthritis & Rheumatism 46:2549-2552, 2002.*
Garnero et al. "Association of Baseline Levels of Markers of Bone and Cartilage Degradation with Long-Term Progression of Joint Damage in Patients with Early Rheumatoid Arthritis" Arthritis & Rheumatism 46:2847-2856, 2002.*
Moller, H. J. "Connective Tissue Markers Of Rheumatoid Arthritis", Scand. J. Clin. Lab. Invest. 1998, 58: 269-278.
Stucki, G., et al. "Management Of Rheumatoid Arthritis", 1997, Current Opinion in Rheumatology, 9: 229-235.
Morein, B., et al. "Iscom, A Novel Structure For Antigenic Presentation Of Membrane Proteins From Enveloped Viruses", Nature, vol. 308, (Mar. 29, 1984), pp. 457-460.
Goding, J. W., "Production Of Monoclonal Antibodies: Principles And Practice", (1986), pp. 59-103.
Ishikawa, E., et al. "Enzyme-Labeling Of Antibodies And Their Fragments For Enzyme Immunoassay And Immunohistochemical Staining", Journal of Immunoassay, 4(3), (1983), pp. 209-327.
Hermanson, Greg T. "Bioconjugate Techniques" 1996, Academic Press, San Diego, USA, pp. 193-196.
Neidhart, M., et al. "Small Fragments Of Cartilage Oligomeric Matrix Protein In Synovial Fluid And Serum As Markers F Cartilage Degradation", British Journal Of Rheumatology 1997, vol. 36, pp. 1151-1160.
Lorenzo, P., et al. "A Novel Cartilage Protein (CILP) Present In The Mid-Zone Of Human Articular Cartilage Increases With Age", J. Biol. Chem. , vol. 273, No. 36, Issue of Sep. 4, 1998, pp. 23463-23468.
Lorenzo, P., et al. "Cloning And Deduced Amino Acid Sequence Of A Novel Cartilage Protein (CILP) Identifies A Proform Including A Nucleotide Pyrophosphohydrolase", J. Biol. Chem., vol. 273, No. 36, Issue of Sep. 4, 1998, pp. 23469-23475.
Kohler, G., et al. "Continuous Cultures Of Fused Cells Secreting Antibody Of Predefined Specificity", Nature, vol. 256, Aug. 7, 1975, pp. 495-497.

(Continued)

*Primary Examiner*—Long V. Le
*Assistant Examiner*—Christine Foster
(74) *Attorney, Agent, or Firm*—Greg B. Butler; Edwards Angell Palmer & Dodge LLP

(57) ABSTRACT

Disclosed are compositions and methods for performing an immuno-assay that includes measuring the amount of an isomerised or optically inverted non-collagen protein derived from cartilage.

2 Claims, 8 Drawing Sheets

OTHER PUBLICATIONS

Rosenquist, C., et al. "Serum Crosslaps One Step ELISA. First Application Of Monoclonal Antibodies For Measurement In Serum Of Bone-Related Degradation Products From C-Terminal Telopeptides Of Type I Collagen", Clinical Chemistry (1998), vol. 44, No. 11, pp. 2281-2289.

Kearney, J. F., et al. "A New Mouse Myeloma Cell Line That Has Lost Immunoglobulin Expression But Permits The Construction Of Antibody-Secreting Hybrid Cell Lines", Journal of Immunology, vol. 123, No. 4 , Oct. 1979, pp. 1548-1550.

Maroudas. A., et al. "Aggrecan Turnover In Human Articular Cartilage: Use Of Aspartic Acid Racemization As A Marker Of Molecular Age", Archives Of Biochemistry And Biophysics, vol. 350, No. 1, Feb. 1, 1998, pp. 61-71.

Hughes, C. E., et al. "Monoclonal Antibodies That Specifically Recognize Neoepitope Sequences Generated by 'Aggrecanase' And Matrix Metalloproteinase Cleavage Of Aggrecan: Application To Catabolism In Situ And In Vitro", J. Biochem, (1995), vol. 305, pp. 799-804.

Saxne, T., et al. "Cartilage Oligomeric Matrix Protein: A Novel Marker Of Cartilage Turnover Detectable In Synovial Fluid And Blood", British Journal Of Rheumatology 1992, vol. 31, pp. 583-591.

Wollheim F.A. "Predictors Of Joint Damage In Rheumatoid Arthritis", 1996, APMIS 104: 81-93.

Geiger, T., et al. "Deamidation, Isomerization, And Racemization At Asparaginyl And Aspartyl Residues In Peptides", J. Biol. Chem. , vol. 262, No. 2, Jan. 15, 1987, 785-794.

Clarke, S. "Propensity For Spontaneous Succinimide Formation From Aspartyl And Asparaginyl Residues In Cellular Proteins", Int. J. Peptide Protein Res.. 30: 1987, 808-821.

Poole, A. R., et al. "Biological Markers In Rheumatoid Arthritis", Seminars In Arthritis And Rheumatism, vol. 23, No. 6, Suppl 2 Jun. 1994, pp. 17-31.

Fledelius, C. , et al. "Characterization Of Urinary Degradation Products Derived From Type I Collagen", J. Biol. Chem., vol. 272, No. 15, Apr. 11, 1997, pp. 9755-9763.

Glant, T., et al. "Progressive Polyarthritis Induced In BALB/c Mice By Aggrecan From Normal And Osteoarthritic Human Cartilage", Arthritis & Rheumatism, vol. 41, No. 6. Jun. 1998, pp. 1007-1018.

Dudhia, J., et al. "Age-Related Changes In The Content Of The C-Terminal Region Of Aggrecan In Human Articular Cartilage", Biochem. J. 313, 1996, pp. 933-940.

Zhang, Y., et al. "Induction Of Arthritis In BALB/c Mice By Cartilage Link Protein", Amer. Journal Of Pathology, vol. 153, No. 4, Oct. 1998, pp. 1283-1291.

Radkiewicz, J. L., et al. "Accelerated Racemization Of Aspartic Acid And Asparagine Residues Via Succinimide Intermediates: An Ab Initio Theoretical Exploration Of Mechanism", J. Amer. Chem. Soc. ,1996, 118, pp. 9148-9155.

Rafferty, B., et al. "Pharmacokinetic Evaluation Of Superactive Analogues Of Growth Hormone-Releasing Factor (1-29)-Amide", Peptides, vol. 9, pp. 207-209, 1988.

Van Regenmortel, M., et al. "D-Peptides As Immunogens And Diagnostic Reagents", Current Opinion In Biotechnology, vol. 9: , pp. 377-382, 1998.

Campbell, A.M. "Monoclonal Antibody And Immunosensor Technology", Laboratory Techniques In Biochemistry And Molecular Biology, vol. 23 (1991), pp. 136-205.

* cited by examiner

SEQUENCE LISTING

<160> NUMBER OF SEQ ID NOS: 10

<210> SEQ ID NO 1
<211> LENGTH: 6
<212> TYPE: PRT
<213> ORGANISM: Homo sapiens

-continued

<400> SEQUENCE: 1

Asn Ile Thr Glu Gly Glu
 1               5

<210> SEQ ID NO 2
<211> LENGTH: 6
<212> TYPE: PRT
<213> ORGANISM: Homo sapiens

<400> SEQUENCE: 2

Ala Arg Gly Ser Val Ile
 1               5

<210> SEQ ID NO 3
<211> LENGTH: 6
<212> TYPE: PRT
<213> ORGANISM: Homo sapiens

<400> SEQUENCE: 3

Val Asp Ile Pro Glu Asn
 1               5

<210> SEQ ID NO 4
<211> LENGTH: 9
<212> TYPE: PRT
<213> ORGANISM: Homo sapiens

<400> SEQUENCE: 4

Gly Arg Val Arg Val Asn Ser Ala Tyr
 1               5

<210> SEQ ID NO 5
<211> LENGTH: 13
<212> TYPE: PRT
<213> ORGANISM: Homo sapiens

<400> SEQUENCE: 5

Ala Gly Trp Leu Ala Asp Gly Ser Val Arg Tyr Pro Ile
 1               5                   10

<210> SEQ ID NO 6
<211> LENGTH: 9
<212> TYPE: PRT
<213> ORGANISM: Homo sapiens
<220> FEATURE:
<221> NAME/KEY: MOD_RES
<222> LOCATION: (6)
<223> OTHER INFORMATION: alpha-D Asp, Asn or beta-L or beta-D Asp

<400> SEQUENCE: 6

Gly Arg Val Arg Val Asx Ser Ala Tyr
 1               5

<210> SEQ ID NO 7
<211> LENGTH: 15
<212> TYPE: PRT
<213> ORGANISM: Homo sapiens
<220> FEATURE:
<221> NAME/KEY: MOD_RES
<222> LOCATION: (9)
<223> OTHER INFORMATION: alpha-D Asp, Asn or beta-L or beta-D Asp

<400> SEQUENCE: 7

Tyr Leu Ala Trp Gln Ala Gly Met Asx Met Cys Ser Ala Gly Trp
 1               5                   10                  15

```
<210> SEQ ID NO 8
<211> LENGTH: 10
<212> TYPE: PRT
<213> ORGANISM: Homo sapiens
<220> FEATURE:
<221> NAME/KEY: MOD_RES
<222> LOCATION: (6)
<223> OTHER INFORMATION: alpha-D Asp, Asn or beta-L or beta-D Asp

<400> SEQUENCE: 8

Ala Gly Trp Leu Ala Asx Gly Ser Val Arg
 1               5                  10

<210> SEQ ID NO 9
<211> LENGTH: 9
<212> TYPE: PRT
<213> ORGANISM: Homo sapiens
<220> FEATURE:
<221> NAME/KEY: MOD_RES
<222> LOCATION: (6)
<223> OTHER INFORMATION: beta Asp

<400> SEQUENCE: 9

Gly Arg Val Arg Val Asp Ser Ala Tyr
 1               5

<210> SEQ ID NO 10
<211> LENGTH: 8
<212> TYPE: PRT
<213> ORGANISM: Homo sapiens

<400> SEQUENCE: 10

Glu Lys Ala His Asp Gly Gly Arg
 1               5
```

ASSAY OF ISOMERISED AND/OR OPTICALLY INVERTED PROTEINS AND PROTEIN FRAGMENTS

This application is a continuation of International Application PCT/EP00/11720, with an international filing data of Nov. 24, 2000 and claim the benefit of U.S. Provisional Application No. 60/343,384, filed on Dec. 21, 2001, now abandoned.

BACKGROUND OF THE INVENTION

The present invention relates to immunoassays for non-collagen cartilage proteins and their fragments in biological samples such as a body fluids. Such proteins and protein fragments may serve as an index of joint disease.

Rheumatoid arthritis (RA) is a severe chronic and progressive disease affecting approximately 1% of the population in both the industrialised and the developing world (Harris 1993). Although both environmental, genetic and developmental factors have been implicated in the aetiology of RA, it is now generally accepted that RA is an autoimmune disease. Osteoarthritis (OA) is a chronic disease affecting more than 8% of the population in the industrialised world. This disease also affects the articular cartilage of joints, and although an immune component has been observed as part of the disease pathophysiology, OA is not viewed as an autoimmune disease.

The major clinical manifestation of RA as well as OA is an abnormal and degraded cartilage. However, until now it has been difficult to directly assess the ongoing cartilage destruction in arthritis patients, because specific markers for this process have not been available in the clinical practice (Møller 1998). At clinical diagnosis of RA, the patients are scored according to the disease symptoms and function impairment such as pain, and mobility problems caused by the joint destruction. Even though a number of standardised rating systems have been introduced, it is difficult to quantify these parameters (Stucki et al 1997). Other markers used for assessment of RA patients, such as C-reactive protein and Rheumatoid factors are specific for the inflammatory process involved in the disease, but are not directly related to the level of cartilage destruction and they are not specific for RA (Wollheim 1996). At present one of the best ways to obtain information about the status of the (individual) joints in arthritis patients is radiological examinations.

Measurement of metabolites, such as hyaluronates and aggrecan fragments arising from destruction of the joints affected by the disease have been reported (Møller 1998, Wollheim 1996). The clinical usefulness of these markers, however, remains to be proven.

This invention is based upon a new approach for identifying markers of cartilage degradation, and for development of diagnostic and prognostic assays for monitoring joint diseases. We have shown that specific components of articular cartilage are prone to isomerisation and/or optical inversion (FIG. 1) and we have identified specific isomerisation/optical inversion prone sites in several cartilage proteins. We have also demonstrated that isomerised and/or optically inverted fragments of cartilage protein are found in circulation, and that measurements of such fragments provide an index of joint cartilage degradation.

Aspartic acid and asparagine (Asx) and glutamic acid and glutamine (Glx) residues will in some susceptible proteins undergo a spontaneous re-arrangement where the normal peptide bond between the Asx and Glx residue and the adjacent residue is transferred from the normal α-carboxyl group to the β-carboxyl group (γ-carboxyl group for the Glx residues) of the side chain (Clarke 1987). The isomerisation reaction proceeds via an imide intermediate, which upon spontaneous hydrolysis may result in one of four forms: the normally occurring αL, the isoform βL, or the two optically inverted forms αD and βD as outlined in the following reaction scheme for aspartic acid-glycine. (The reaction occurs analogously for other susceptible Asx and Glx containing sequences):

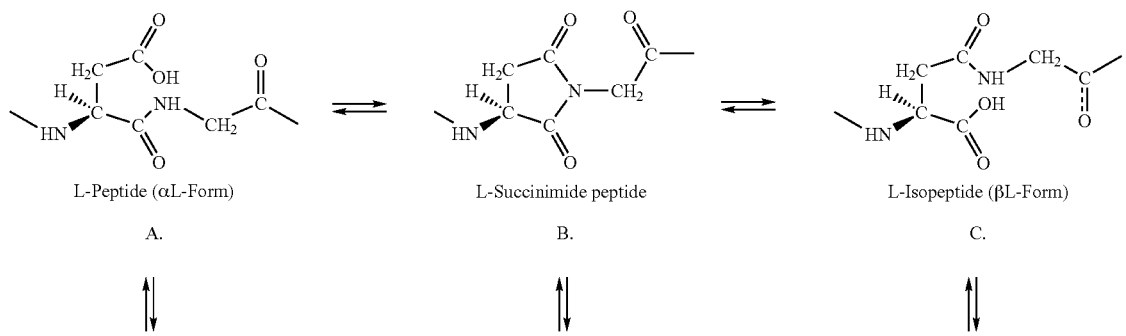

L-Peptide (αL-Form)   L-Succinimide peptide   L-Isopeptide (βL-Form)

A.   B.   C.

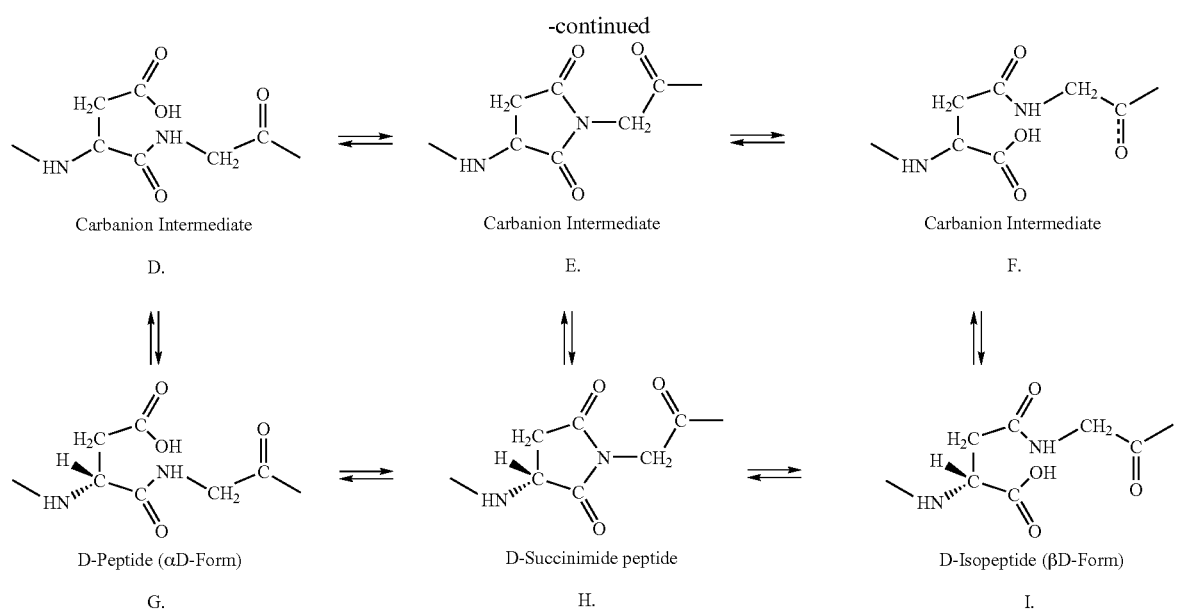

The attack by the peptide backbone nitrogen on the side chain carbonyl group of an adjacent aspartyl residue can result in the formation of an imide ring, (A→B). The imide ring is prone to hydrolysis and optical inversion yielding peptides and isopeptides in both the D and L configurations. Optical inversion proceeds through a carbanion intermediate (D, E and F) either through direct proton abstraction (A↔D↔G or C↔F↔I) or via the imide pathway (B↔E↔H). Throughout the figure the peptide backbone is shown as a bold line.

However, in order for cyclic imide formation (and isomerisation/optical inversion) to occur, the three dimensional structure surrounding the Asx or Glx residues must have an optimal conformation and sufficient flexibility (Geiger and Clarke 1987).

Studies indicate that optical inversion of Asx residues in peptides and proteins primarily proceeds through the imide pathway (B↔E↔H) (Geiger and Clarke 1987, Radkiewics et al. 1996). However, other pathways such as direct proton abstraction or imino-δ-lactone formation may also contribute to optical inversion (Radkiewics et al. 1996). These pathways are however assumed to be of less importance (Geiger and Clarke 1987, Radkiewics et al 1996).

Isomerisation and optical inversion via the imide intermediate as outlined above is a spontaneous reaction occurring with a slow rate under physiological conditions (Geiger & Clarke 1987, Fledelius et al. 1997). As for all chemical reactions, the reaction speed can be accelerated by increasing temperature.

The introduction of such structural changes in a protein or peptide has profound effects on its function, stability and physical and chemical properties. Among other properties, the proteolytic degradation of proteins and peptides containing isomerised peptide bonds and/or optically inverted amino acids is significantly reduced compared to proteins and peptides composed exclusively of αL amino acids (Rafferty et al. 1988) Thus, protein fragments containing such modifications are not degraded to the same extent during normal tissue turnover (Van Regenmortel & Muller 1998) and they are much more likely to be present in circulation in measurable concentrations. Furthermore, by measuring proteins or protein fragments containing isomerised and/or optically inverted peptide linkages, newly synthesised molecules will not contribute to the measurements, and it will thus reflect ongoing degradation processes.

In WO96/30765, we disclosed that isomerised fragments of Type I collagen provided an improved index of bone resorption. It was further disclosed that Type II collagen (as found in cartilage) also contained potential isomerisation sites.

We have demonstrated that articular cartilage, a tissue with a very slow metabolism, contain non-collagen proteins which are subject to isomerisation and optical inversion and we have demonstrated that measurement of these proteins, or fragments thereof, can provide an index of joint cartilage degradation of diagnostic potential for assessing and monitoring joint diseases such as RA and OA.

BRIEF SUMMARY OF THE INVENTION

The present invention provides a method of assay, comprising measuring in a biological sample such as a body fluid or tissue sample the amount of an isomerised or optically inverted non-collagen protein derived from cartilage or of one or more isomerised or optically inverted fragments from such a protein.

Proteins of particular interest include aggrecan and Cartilage link protein.

Aggrecan is a major structural component of articular cartilage, and has been studied for the potential as a biomarker for assessment of joint disease, as well as for a putative role as an autoantigen in RA and animal models of the disease (Poole & Dieppe 1994, Glant et al. 1998).

The protein is a heavily glycosylated large protein comprising more than 2000 amino-acid residues. Aggrecan is structurally organised in three distinct domains: G1, G2 and G3. The G1 domain is commonly mentioned as the primary immunogenic domain in aggrecan (Glant et al. 1998). This globular domain serves as "linker" to the hyaluronic acid polymer, and is also in contact with the Cartilage link protein (CLP). Characteristic epitopes which have been identified as targets for the immune system in animal models of arthritis and also as specific cleavage sites for aggrecanase or stromelysin in the G1 domain are: . . . N$_{\beta 68}$)ITEGE (SEQ ID NO: 1) (containing a consensus sequence for N-linked glycosylation); $_{374}$ARGSVI . . . (SEQ ID NO: 2); . . . VDIPEN$_{341}$ (SEQ ID NO: 3) (Dudhia et al. 1996). Furthermore, it has been described that aspartic acid in aggrecan is susceptible to racemization (Maroudas et al. 1998).

We have identified the asparagine residue in the epitope GRVRVNSAY (SEQ ID NO: 4) from the G1 domain of aggrecan (denoted AG1-1) as an isomerisation/optical inversion susceptible site. In the examples below, we present experimental and clinical data supporting the clinical value of measurements of isomerised and/or optically inverted AG1-1 for monitoring RA.

Cartilage link protein (CLP) is associated with hyaluronan and aggrecan, and probably serves an important function in anchoring aggrecan firmly to the hyaluronan polymers. The molecule binds to the G1 domain of aggrecan, and it also shares structural similarities with this protein (Poole & Dieppe 1994). Cartilage link protein has received little attention as a potential marker of cartilage destruction, but autoimmunity against this cartilage protein has been shown to induce RA in an animal model of the disease (Zhang et al. 1998). However, the protein may be a good marker of the late destruction, occurring when the aggrecan has been degraded to a sufficient extent for allowing access to the link protein (and G1 domains). The link protein is also capable of inducing autoimmune arthritis in rodents, and immunodominant epitopes have been localised to the N-terminus of the protein as well as to the two regions shared by aggrecan (and hyaluronan binding proteins of the Central Nervous System (CNS), such as neurocan and brevican/BEHAB), which contains the putative consensus sequences for hyaluronan binding. One of these sequences has been selected for use as exemplification herein. A potential isomerisation site is underlined. An amino acid difference (conservative substitution) to the G2 domain of aggrecan is indicated in bold:

```
AGWLADGSVRYPI         (SEQ ID NO:5)
```

Cartilage oligomeric matrix protein (COMP) is a non-collagenous glycoprotein (Neidhart et al. 1997). Its physiological role is uncertain. Increased levels of COMP have been seen in early OA and in RA patients with early, rapidly progressive joint destruction, decreasing later.

Cartilage intermediate layer protein (CILP) is non-collagenous cartilage protein composed of a single polypeptide chain with a molecular weight of 91.5 kDa, including N-linked oligosaccharides (Lorenzo et al. 1998a and 1998b).

The protein is synthesized by chondrocytes and located to the interterritorial cartilage. It is neither found in the superficial nor deepest regions of the articular cartilage. CILP has been reported to increase with age and has been suggested to be a marker of early OA.

Preferably, the method determines the amount of at least one *Asx or *Glx containing protein or protein fragment in said biological sample, wherein *Asx is αD Asp or Asn or is βL or βD Asp and *Glx is αD Glu or Gln or γL or γD Glu.

Preferably, there is a glycine or serine adjacent the Asx/Glx in the native protein, as this facilitates isomerisation or optical inversion.

Said protein is preferably aggrecan, CLP, COMP, or CILP or said fragment is a fragment of aggrecan, CLP, COMP, or CILP.

Preferably the method measures the amount of at least one protein or protein fragment containing the aggrecan derived amino acid sequence: Gly-Arg-Val-*Asx-Ser-Ala-Tyr (SEQ ID NO: 6), or the amount of at least one protein or protein fragment containing the aggrecan derived amino acid sequence:

Tyr-Leu-Ala-Trp-Gln-Ala-Gly-Met-*Asx-Met-Cys-Ser-Ala-Gly-Trp (SEQ ID NO: 7), or the amount of at least one protein or protein fragment containing the CLP derived amino acid sequence:

Ala-Gly-Trp-Leu-Ala-*Asx-Gly-Ser-Val-Arg (SEQ ID NO: 8).

Said measurement is Preferably carried out using an immunological binding partner which specifically binds an amino acid sequence comprising *Asx or *Glx flanked by amino acid residues of a non-collagen cartilage protein. The immunological binding partner should discriminate between the sequence containing *Asx or *Glx and the corresponding sequence containing αL Asx or αL Glx to a degree adequate to provide a useful assay. The cross-reactivity of assay/antibody towards the corresponding αL-form of the antigen/epitope should be less than 25%, preferably less than 5%.

Suitably, the immunological binding partner is an antibody raised against a synthetic peptide having an amino acid sequence comprising *Asx or *Glx flanked by amino acid residues of a non-collagen cartilage protein, or fragments of such an antibody having immunological binding specificity to said peptide.

The amino acid sequence of the peptide therefore preferably corresponds to a characteristic sequence of said protein, with *Asx or *Glx substituting for αL Asp, Asn, Gln, or Glu in said protein sequence, i.e. to a sequence essentially unique to the protein in question. Suitably the peptide is from 6 to 50 amino acids in length, e.g. from 6 to 15 amino acids in length.

The measurement may be used to provide an index of joint disease. This may serve as an aid to initial diagnosis or assessment of severity or to monitor the effect of a treatment.

The invention includes a method as described above further comprising carrying out a measurement of a second index of joint disease and determining the value of a parameter mathematically combining said two indices. The second index may also be derived by a method according to this invention.

The invention includes the use in an assay of an isomerised or optically inverted non-collagen protein derived from cartilage or of one or more isomerised or optically inverted fragments from such a protein. The invention also includes the use of an immunological binding partner which specifically binds an amino acid sequence comprising *Asx or *Glx flanked by amino acid residues of a non-collagen cartilage protein in an in vitro method for the diagnosis or the assessment of the severity of OA or RA.

The invention further provides an immunological binding partner which specifically binds an amino acid sequence comprising *Asx or *Glx flanked by amino acid residues of a non-collagen cartilage protein. The invention further includes a cell line producing a monoclonal antibody which is such an immunological binding partner.

The invention further provides a peptide, preferably of up to 50 amino acid residues, more preferably of up to 20, e.g. of 6 to 50 or more preferably of 6 to 15, amino acids in length containing *Asx or *Glx flanked by amino acid residues of a non-collagen cartilage protein and the use of such a peptide in an assay for protein or protein fragments.

The invention includes a method of immunoassay in which a biological sample is contacted with an immunological binding agent in the presence of such a peptide acting as a competition agent for binding to said immunological binding agent.

The invention includes a test kit comprising (a) an immunological binding partner as defined above or (b) a peptide as described in combination the other of (a) or (b) and optionally in combination with one or more of apparatus in which to perform an immunoassay, an antibody-enzyme conjugate, a substrate for an enzyme component of an antibody-enzyme conjugate, an enzyme-substrate reaction stopping composition, a wash solution, a carrier bound to said binding partner or a detectable label bound to said binding partner.

The invention is not limited to enzyme-immunoassays but includes any procedures for immunoassay known in the art.

The immunological binding partner may be a monoclonal or polyclonal antibody.

Suitable immunological binding partners also include fragments of antibodies capable of binding the same antigenic determinant including Fab, Fab' and F(ab')$_2$ fragments.

The assay may take many forms including ELISA, RIA, or IRLMA, procedures for which are too well known to warrant description here. The assay may be in homogeneous or heterogeneous format.

In a competition assay, a peptide as described above may be used to compete for an immunological binding partner with one or more isomerized or optically inverted proteins or peptides in the sample. In an ELISA of this type, an isomerised and/or optically inverted synthetic peptide may be immobilised on a solid support. A sample may be incubated with a monoclonal, or polyclonal antibody reactive with the synthetic peptide in contact with the solid support and after washing, a peroxidase-conjugated (revealing) antibody may be added. After further incubation, a peroxidase substrate solution is added. By competition, isomerised or optically inverted protein or peptide in the sample reactive with the antibody inhibits the peroxidase reaction.

Alternatively, the synthetic peptide may be used to raise a monoclonal immunological binding partner. The synthetic peptide need not then be a competing agent in the assay. For instance, enzymatically fragmented cartilage protein (such as aggrecan) may be purified and immobilised onto the solid support and an ELISA may be carried out using a monoclonal antibody.

The invention may be applied both to humans and to animals.

Suitable body fluids include, human or animal urine, blood, serum, plasma and synovial fluid. It is contemplated that the method may also be used e.g. on saliva and sweat. The body fluid may be used as it is, or it may be purified prior to the contacting step. This purification step may be accomplished using a number of standard procedures, including, but not limited to, cartridge adsorption and elution, molecular sieve chromatography, dialysis, ion exchange, alumina chromatography, hydroxyapatite chromatography, and combinations thereof.

The preparation of synthetic peptides containing an isomerised peptide bond and/or optically inverted amino acid residue may be performed according to procedures well known in the art, e.g. by solid-phase peptide synthesis techniques commonly described as "Merrifield synthesis".

Also classical solution phase techniques may be used. The conventional peptide synthesis method may produce a mixture of the various peptide isoforms (αL, βL, αD, βD, γL, γD). Generally such a mixture will be satisfactory as the normal peptide will be inert in the assay. However, heating of a pure preparation of the αL-form will generate isomerised, optically inverted isoforms.

The methods for preparation of both monoclonal and poly-clonal antibodies are well known in the art. For example, see Campbell 1986. It is possible to produce antibodies to synthetic isomerized and/or optically inverted peptides by immunisation. However, because of the relatively small molecular weight of these compounds it is preferred that the hapten be conjugated to a carrier molecule. Suitable carrier molecules include, but are not limited to, bovine serum albumin, thyroglobulin, ovalbumin, tetanus toxoid, and keyhole limpet hemocyanin. The preferred carrier is bovine serum albumin or thyroglobulin. To present the hapten in its most immunogenic form to the antibody producing cells of the immunised animal a number of alternative coupling protocols can be used. Suitable procedures include, but are not limited to, glutaraldehyde, carbodiimide, and periodate. Preferred binding agents are glutaraldehyde and carbodiimide.

The preparation of antibodies may be carried out by conventional techniques including immunisation with protein fragments containing natural isomerization and/or optical inversion or synthetic peptides conjugated to a carrier. To improve the immunogenicity it is preferred that the immunogen be mixed with an adjuvant before injection. Examples of adjuvants include, but are not limited to, aluminium hydroxide, Freund's adjuvant, and immune-stimulating complexes (ISCOMs). ISCOMs can be made according to the method described by Morein 1984.

Either monoclonal or polyclonal antibodies to the hapten-carrier molecule can be produced. For the production of monoclonal antibodies it is preferred that mice are immunised. Spleen cells from the immunised mouse are harvested, homo-genised, and thereafter fused with cancer cells in the presence of polyethylene glycol to produce a cell hybrid which produces monoclonal antibodies specific for isomerized and/or optically inverted peptide fragments. Suitable cancer cells include, but are not limited to, myeloma, hepatoma, carcinoma, and sarcoma cells. Detailed descriptions of the production of monoclonal antibodies are provided in Goding 1986. A preferred preliminary screening protocol comprises the use of synthetic isomerized and/or optically inverted peptides conjugated to a carrier and coated on to the solid surface of a microtitre plate.

For the preparation of polyclonal antibodies, which are reactive with isomerized and/or optically inverted peptide fragments, different animal species can be immunised. Suitable species include, but are not limited to, chicken, rabbit and goat. Chicken and rabbit are preferred.

Antibodies so produced may be screened for suitability for use according to the invention by testing for reactivity with an isomerised and/or optically inverted synthetic peptide of appropriate sequence.

Antibody fragments are prepared by methods known in the art (Ishikawa 1983).

Accordingly, by utilisation of an immunoassay with the antibodies prepared as above it is possible to assay a bio-logical sample such as a body fluid without prior fractionation or hydrolysis. The specificity for the desired fragments in the biological fluid may be supplied by the antibody in combination with the use of a synthetic isomerized and/or optically inverted peptide (against which the antibody was raised or in any event with which the antibody is immunochemically reactive) in the assay construction.

As an alternative the immunoassay may be performed using a monoclonal antibody. This assay design shifts the specificity of the assay from the antigen (synthetic peptide isomer of the protein) to the antibody (from rabbit antiserum to monoclonal antibody). Using this construction the assay does not need to make further use of a synthetic peptide isomer. This version of the immunoassay is suitably performed by incubating the patient sample or a standard solution with a peroxidase-conjugated antibody solution in a microtiter plate precoated with purified protein, protein fragments, synthetic peptides or conjugates thereof. After washing, the wells of the plate are incubated in the dark with a substrate solution. The colour reaction is stopped by the addition of a stopping solution, and finally the absorbance is measured. Alternatively one or more monoclonal antibodies may be used in a sandwich assay format.

The immunoassays themselves may be conducted using any procedure selected from the variety of standard assay protocols generally known in the art. As it is generally understood, the assay is constructed so as to rely on the interaction between the specific immunological binding partner and the desired analyte for specificity and to utilise some means to detect the complex formed by the analyte and the immuno-logical binding partner. The immunological binding partner may be complexed to a solid support and used as a capture immunological binding partner for the analyte. This protocol may be run in a direct form, wherein the formation of analyte-immunological binding partner complex is detected, e.g. by a fluorescent, radioactive or enzymatic label, or it may be run in a competitive format wherein a labelled standard competes with the analyte for the immunological binding partner. The format may also be constructed as an agglutination assay or the complex may be precipitated by addition of a suitable precipitant to the reaction mixture. The specific design of the immunoassay protocol is open to a wide variety of choice, and the number of clinical assay devices and protocols available in the art is multitudinous. For a variety of such protocols, see U.S. Pat. No. 5,001,225.

The antibodies and revealing reagents for the conduct of an immunoassay using standard detection protocols, for example radioisotope labelling, fluorescent labelling or ELISA, either in a direct or competitive format, may conveniently be supplied as kits which include the necessary components and instructions for the assay. In one embodiment of the invention such a kit includes a microtiter plate coated with a relevant synthetic isomerized or optically inverted peptide, standard solutions for preparation of standard curve, a body fluid (e.g. urine) control for quality testing of the analytical run, rabbit antibodies reactive with the above mentioned synthetic peptide isomer, anti-rabbit immuno-globulins conjugated to peroxidase, a substrate solution, a stopping solution, a washing buffer and an instruction manual.

Since immunoassays can be constructed using antibodies and specific synthetic isomerized peptides, the ratios of the corresponding protein fragment sequences in an appropriate biological fluid can be determined as well as their individual levels and their total amount. Thus, the assay can be designed to include antibodies which will result in determination of several isomerised and/or optically inverted peptides and optionally the native peptide sequences or determination of a single isomerised and/or optically inverted peptide sequence, or any desired combination thereof.

The invention will be further described and illustrated by the following non-limiting examples in which reference is made to the accompanying drawings, in which:—

EXAMPLE 1

Isomerisation of Synthetic AG1-1 Peptides

The AG1-1 peptide GRVRVNSAY (SEQ ID NO: 4) was synthesised, and dissolved in phosphate buffered saline to 1 mg/ml. The peptide solution was heated to 90° C. for 4 hours to promote isomerisation/optical inversion. Reverse-phase HPLC was performed to analyse the peptide preparations before and after heating.

Figure 1:
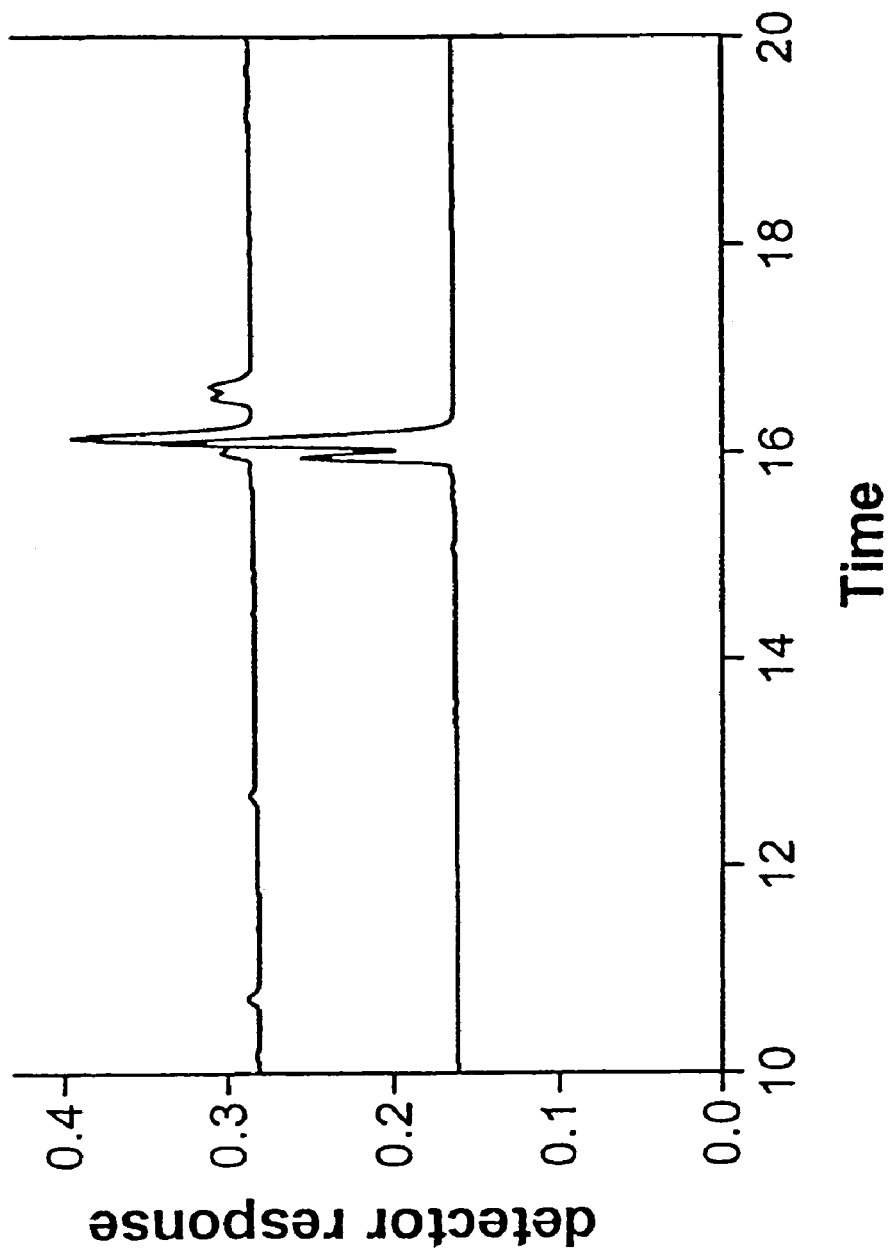
FIG. 1 shows HLPC traces showing the effect of heating a synthetic peptide in generating isomerised and optically inverted peptide forms.

FIG. 1 shows the results of RP-HPLC of a 1 mg/ml AG1-1 peptide preparation before (lower trace) and after (upper trace) heating at 90° C. for 4 hours.

This demonstrates that heating induces 3 new forms of the peptide with retention times in RP-HPLC in accordance with βL, αD and βD forms.

EXAMPLE 2

Generation of Antisera for a βL form of an Epitope Derived from the G1 Domain of Aggrecan and Analysis of Specificity A CDI conjugate of the AG1-1 peptide was prepared essentially according to Hermanson 1996. Briefly, CDI conjugates are prepared as follows: One-hundred mg of thyroglobulin is dissolved in 10 ml to a concentration of 10 mg/ml in 0.05 M MES, 0.5 M NaCl, pH 6.0. One-hundred µl of the two following reagents (to a final concentration of 4 mM CDI, corresponding to approximately 100 fold molar excess of CDI to thyroglobulin, and 10 mM NHS) is added, and the solution is left to mix 15 min at room temperature (18-22° C.). CDI: 0.4 M CDI stock: 76.7 mg is 1 ml water prepared immediately prior to use. NHS: 1 M sulfo-NHS stock: 217.1 mg in 1 ml water prepared immediately prior to use.

Excess cross-linking reactants are removed by gel-filtration on four NAP25 de-salting columns (Pharmacia, Sweden) into 10 mM Na-Phosphate pH 9.0. The de-salted activated thyroglobulin is pooled and divided into 6 portions of 2 ml. Immediately following the gel-filtration, peptide solutions (2 ml 4 mg/ml in 0.1 M Na-Phosphate pH 9.0) are added to each vial. A control conjugation is carried out with an irrelevant peptide. The coupling reaction is allowed to proceed for two hours at room temperature.

Each conjugate is changed into PBS (pH 7.4) by gel-filtration on SEPHADEX G25 columns (Pharmacia, Sweden), and the concentration is adjusted to 2 mg/ml in PBS.

Rabbits (strain SSC:CPH), are immunised subcutaneously with 1 ml 0.25 mg/ml of the vaccine in phosphate buffered saline (PBS), containing 50% Freunds incomplete adjuvant. Rabbits are boosted after initial immunisations at two week intervals. After the three first boosts, subsequent booster immunisations are performed at one month intervals. Pre-immune bleed is collected before immunisation and test bleeds are collected one week after the $2^{nd}$ immunisation to monitor serum antibody levels. Bleeds are subsequently collected one week after the $5^{th}$ and $6^{th}$ immunisation.

The specificity of the rabbit bleeds are tested on a MTP coated with a 10 ng/ml BSA-BS³-AG1-1 conjugate. The BS³ conjugation is performed as follows:

The AG1-1β peptide (GRVRVβ-DSAY) (SEQ ID NO: 9) is dissolved in freshly filtered PBS to 2 mg/ml. The carrier protein (BSA, Bovine serum albumin) is prepared in 3 mg/ml concentration in PBS. 200 µl of carrier protein is mixed with 200 µl peptide solution in a 1.5 ml polypropylene tube (Eppendorf, Germany). This corresponds to approximately 50 fold molar excess of peptide to carrier protein. BS³ (Bis-(sulfosuccinimidyl)suberate) is prepared freshly in a 6 mg/ml solution in 5 mM sodium-citrate pH 5.0. 50 µl of the cross-linker is added to the carrier and peptide solution, which is vortexed and placed on a mixer at room temperature (this corresponds to fold molar excess of cross-linker compared to carrier protein). After 30 mm incubation, 50 µl 0.25 M glycine pH 7.5 is added to the solutions. The incubation is continued for 15 min., whereafter the conjugates are desalted on NAP5 column (Amersham Pharmacia, Uppsala, Sweden) and protein concentrations are determined.

The rabbit antiserum is diluted in PBS containing 1% BSA and 0.1% Tween in a suitable dilution for obtaining an appropriate ELISA signal. The bound antibody in this competitive assay format is detected by use of a secondary peroxidase conjugated goat anti-rabbit antibody and a chromogenic peroxidase substrate.

A serum assay was developed using an AG1-1 antiserum. This assay was performed as a competitive assay on plates coated with 10 ng/ml BSA-BS³-AG1-1 Twenty µl sample or calibrator is pipeted in the wells followed by addition of 100 µl AG1-1 specific antibody suitably diluted in 300 mM Tris; 0.1% Tween 20; 1% BSA, pH 8.0 (TBT). The plate is incubated for 60 min at 20° C., washed five times in (TBT), and 100 µl of a secondary peroxidase conjugated goat anti rabbit antiserum suitably diluted in 100 mM Tris pH 7.4, 0.4 g/l 4-Amino-anti-pyrine, 0.012% BRONIDOX (bacteriostatic agent), 0.1% Tween 20 and 20% fetal calf serum (K5 buffer) is added to each well. The plate is incubated 60 min at 20° C. washed five times in TBT and the amount of bound antibody is quantified by the use of a chromogenic peroxidase substrate.

Figure 2:
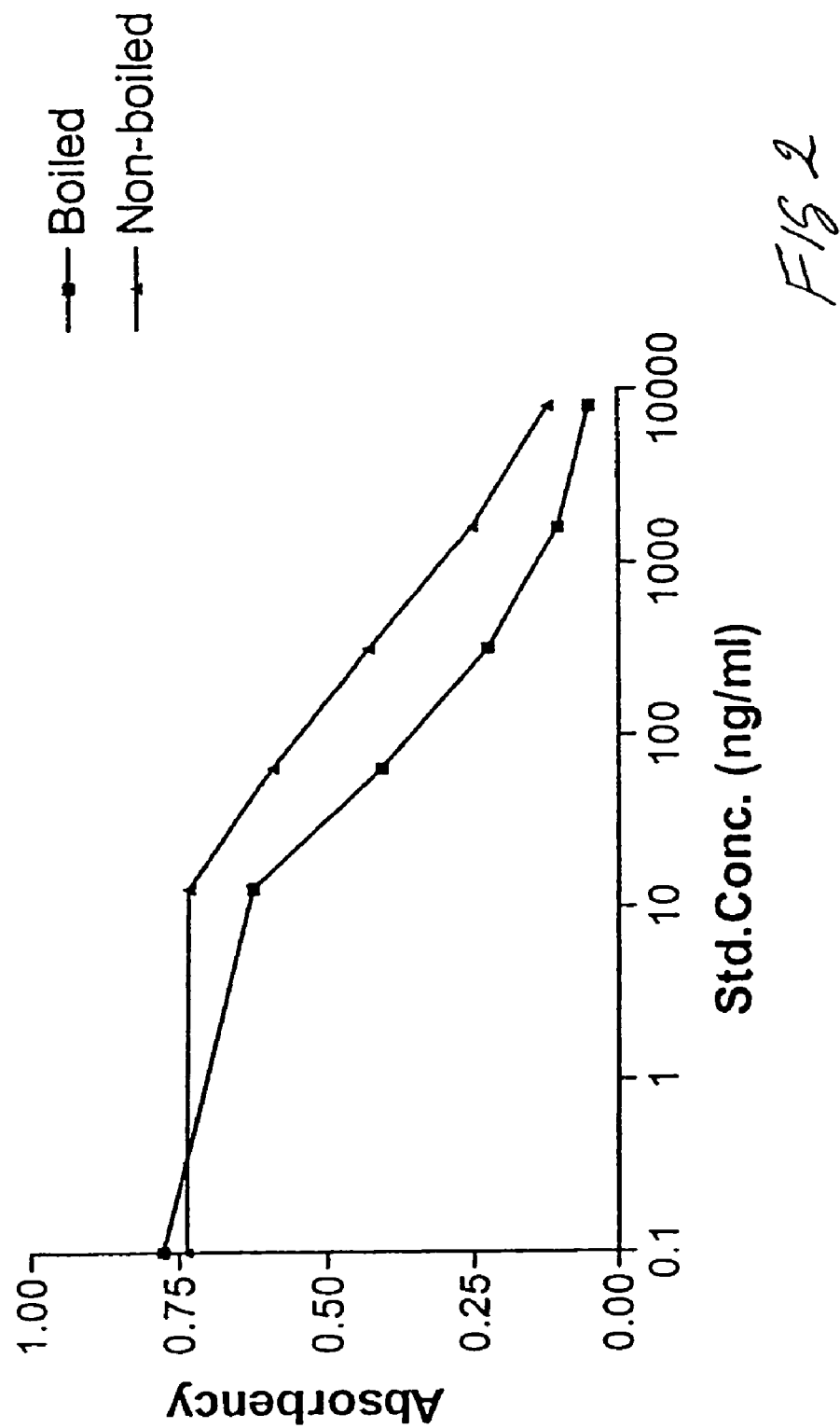
FIG. 2 shows the results of an ELISA (AG1-1 ELISA) demonstrating the specificity for isomerised or optically inverted peptide of a polyclonal rabbit antiserum.

FIG. 2 shows competition of binding in an AG1-1 specific ELISA performed with BSA-BS³-AG1-1 coated plates, a polyclonal AG1-1 specific rabbit antiserum and preparations of AG1-1 peptide subjected to no "boiling" (Triangles) or heating at 90° C. for 4 hours (Squares). The AG1-1 ELISA shows a seven-fold higher reactivity with the "boiled" peptide preparation compared with the non-boiled form.

The preference of the AG1-1 specific antiserum towards the "boiled" form of the peptide suggests that it preferentially recognises one or more of the isomerised and/or optically inverted form (βL, αD or βD).

EXAMPLE 3

Generation of Monoclonal Antibodies Specific for a βL Form of an Epitope Derived from the G1 Domain of Aggrecan and Analysis of Specificity A CDI conjugate of the AG1-1 peptide was prepared essentially according to Hermanson 1996. Briefly described with CDI conjugates are prepared as follows: One-hundred mg of thyroglobulin is dissolved in 10 ml to a concentration of 10 mg/ml in 0.05 M MES, 0.5 ml NaCl, pH 6.0. One-hundred µl of the two following reagents (to a final concentration of 4 mM. CDI, corresponding to approximately 100 fold molar excess of CDI to thyroglobulin, and 10 mM NHS) is added, and the solution is left to mix 15 min at room temperature (18-22° C.). CDI: 0.4 M CDI stock: 76.7 mg is 1 ml water prepared immediately prior to use. NHS: 1 M sulfo-NHS stock: 217.1 mg in 1 ml water prepared immediately prior to use.

Excess cross-linking reactants are removed by gel-filtration on four NAP25 de-salting columns into 10 mM Na-Phosphate pH 9.0. The de-salted activated thyroglobulin is pooled and divided into 6 portions of 2 ml. Immediately following the gel-filtration peptide solutions: 2 ml 4 mg/ml in 0.1 M Na-Phosphate pH 9.0 are added to each vial. A control conjugation is carried out with an irrelevant peptide. The coupling reaction is allowed to proceed for two hours at room temperature.

Each conjugate is changed into PBS (pH 7.4) by gel-filtration on Sephadex G25 columns (Pharmacia, Sweden), and the concentration is adjusted to 2 mg/ml in PBS. Mouse (female strain BalbC×CF1), are immunised subcutaneously with 200 µl 0.125 mg/ml of the vaccine in phosphate buffered saline (PBS), containing 50% Freunds incomplete adjuvant. Mice are boosted after initial immunisations at two-week intervals for a total of 8 weeks. Pre-immune bleed is collected before immunisation and test bleeds are collected one week after the $2^{nd}$ immunisation to monitor serum antibody levels. Bleeds are subsequently collected one week after the $5^{th}$ and $6^{th}$ immunisation.

The specificity of the mouse serum samples were tested on a MTP coated with a 10 ng/ml BSA-BS³-AG1-1 conjugate. The mouse serum was diluted in PBS containing 1% BSA and 0.1% Tween in a suitable dilution for obtaining an appropriate ELISA signal. The bound antibody in this competitive assay format was detected by use of a secondary peroxidase conjugated rabbit anti-mouse antibody and a chromogenic peroxidase substrate.

Monoclonal-antibody producing hybridomas were prepared essentially as described by Köhler and Milstein (22) with the modifications described previously (7,23). Spleen cells from mice were fused with Ag8×63.653 myeloma cells

(24) at a ratio of approximately 2:1 (spleen:myeloma) in the presence of 47% polyethylene glycol (PEG) and 7.5% dimethyl sulphoxide (DMSO). The spleen cells were plated in human endothelial culture supernatant (HACS, Costar, Fla., USA). Following selection in hypoxanthine-aminopterin-thymidine (HAT) containing medium, culture supernatants were screened for antibodies recognizing collagenase digested collagen type II in an indirect ELISA performed essentially as described (7). Selected cell lines were cloned at least three times and propagated in RPMI-1640 media containing 2% fetal calf serum. Monoclonal antibodies were isolated from the culture supernatants by affinity chromatography using protein A chromatography performed according to the manufacturers instructions (Pharmacia, Uppsala, Sweden). Briefly described a 10×1 cm (10 ml) column of Protein A SEPHAROSE 4B was packed and equilibrated in 0.1 M tris pH 8.8. 2 l of culture supernatant is filtered through a Nalgene 0.45 µn filter, and 200 ml of 1 M Tris pH 8.8 is added. The culture supernatant is loaded on the column at 1 ml/min followed by washing of the column with 100-150 ml 0.1 M Tris pH 8.8. Bound immunoglobulins are eluted with 0.1 M glycine pH 3.0 into vials containing 50 µl 1M Tris pH 8.8. The subclass of monoclonal antibodies was determined using the ISOSTRIP™ isotyping kit (Boehringer Mannheim GmbH, Munich, Germany).

A serum assay was developed using an AG1-1 monoclonal antibody (termed MabF49). This assay was performed as a competitive assay on Streptavidin coated microtitre-plates plates (Exiqon, Trørød, Denmark). The plates are washed three times in washing buffer (25 mM Tris, 51 mM NaCl, 0.1% tween 20, pH 7.2) and incubated with 100 µl/well of biotinylated AG1-1βL peptide (biotin-GRVRVβ-DSAY) (SEQ ID NO: 9) diluted to a concentration of 1.25 ng/ml in PBS containing 0.1% tween 20. After 30 in incubation at 20° C. on a shaking table (300 RPM), fifty µl sample or calibrator is pipetted in the wells followed by addition of 100 µl AG1-1 specific monoclonal antibody F49 diluted in:

100 mM Tris, 50 mM MES, 50 mM CaCl2, 5% Sorbitol, 1% BSA, 0.02% Tween 20, 0.4 g/l 4-Amino-anti-pyrine, 0.012% BRONIDOX (bacteriostatic agent) pH 6.0 (assay buffer). The plate is incubated overnight (18-24 hours) at 4° C., washed five times in washing buffer, and 100 µl of a secondary peroxidase conjugated rabbit anti mouse antiserum suitably diluted in assay buffer is added to each well. The plate is incubated 60 min at 20° C. washed five times in TBT and the amount of bound antibody is quantified by the use of a chromogenic peroxidase substrate.

Figure 3:
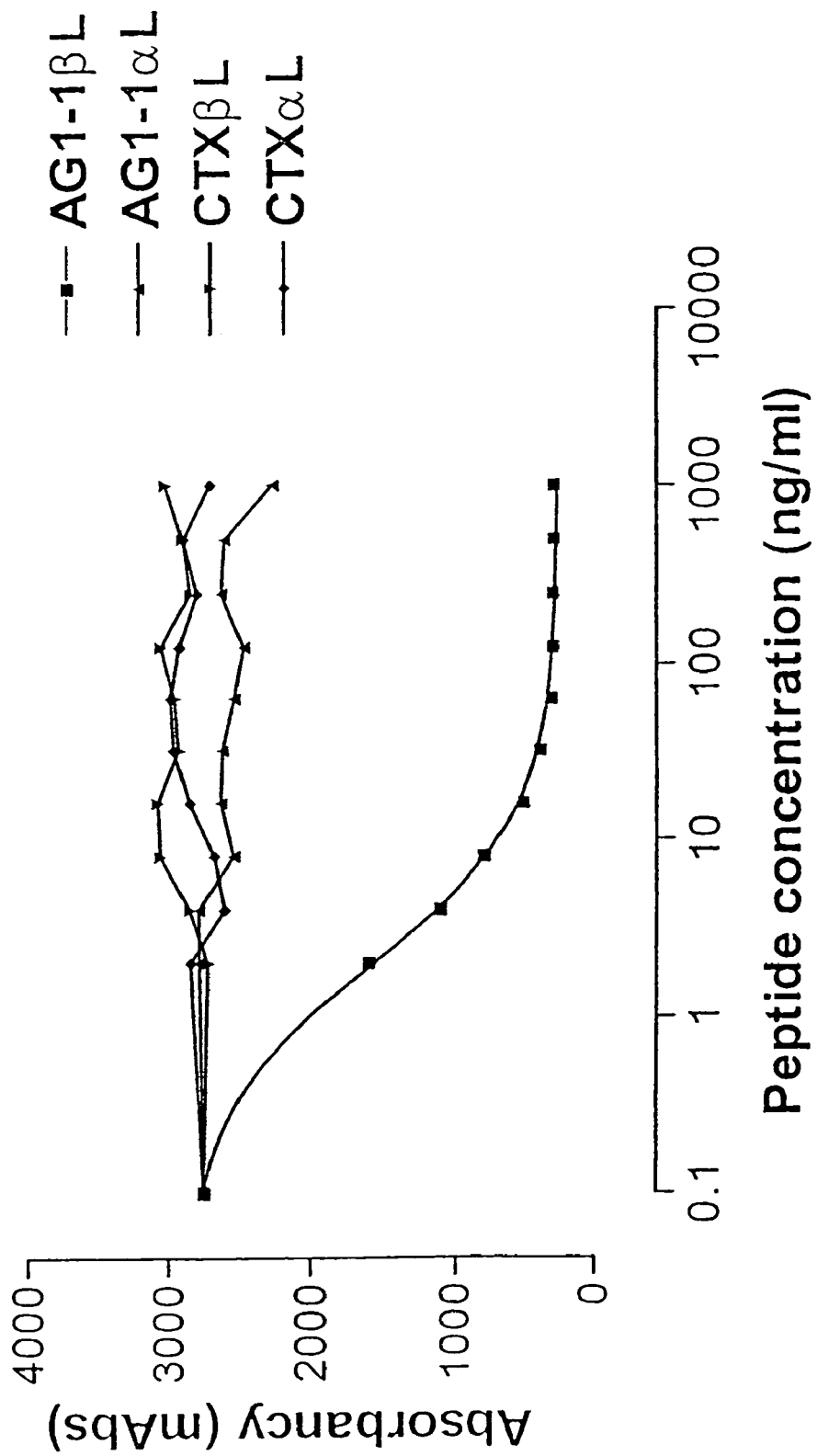
FIG. 3 shows the results of an ELISA (AG1-1 ELISA) demonstrating the specificity for isomerised or optically inverted peptide of a monoclonal rabbit antiserum.

FIG. 3 shows competition of binding in an AG1-1 specific monoclonal ELISA performed as described above and preparations of the non isomerized (αL) and isomerized (βL) forms of the AG1-1 peptide (GRVRVNSAY) (SEQ ID NO: 4) or a control peptide derived from collagen type I C-telopeptides (EKAHDGGR, CTx) (SEQ ID NO: 10). The AG1-1 ELISA shows more than a 500-fold higher reactivity with the isomerized βL peptide preparation compared with the αL form.

EXAMPLE 4

Generation of an Antiserum Specific for a Cartilage Link Protein (CLP) Derived Epitope A CDI conjugate of the CLP derived peptide: Ala-Gly-Trp-Leu-Ala-Asx*-Gly-Ser-Val-Arg (SEQ ID NO: 8) coupled to thyroglobulin was prepared as described in example 2. The CLP peptide was heated at 90° C. for 4 hours prior to the conjugation in order to promote isomerisation and/or optical inversion. The Thy-CDI-CLP conjugate was used for immunization of rabbits as described in example 2.

Separate conjugates were prepared for primary screening of the rabbit bleeds. This was done using a BS³ succinimide covalent cross-linker and BSA as carrier protein (according to: Greg T. Hermanson, 'Bioconjugate techniques' 1996, Academic press, San Diego, USA).

The specificity of the rabbit bleed was tested on a MTP coated with a 10 ng/ml BSA-BS³-CLP conjugate. The rabbit antiserum was diluted in PBS containing 1% BSA and 0.1% Tween in a suitable dilution for obtaining an appropriate ELISA signal. The bound antibody in this competitive assay format was detected by use of a secondary peroxidase conjugated goat anti rabbit antibody and a chromogenic peroxidase substrate.

The best responding rabbit antiserum was selected for development of a CLP specific assay. This assay was performed as a competitive assay on plates coated with 10 ng/ml BSA-BS³-CLP. Twenty µl sample or calibrator is pipeted in the wells followed by addition of 100 µl CLP specific antibody suitably diluted in 300 mM Tris; 0.1% Tween 20; 1% BSA, pH 8.0 (TBT). The plate is incubated for 60 min at 20° C., washed five times in (TBT), and 100 µl of a secondary peroxidase conjugated goat anti rabbit antiserum suitably diluted in K5 buffer is added to each well. The plate is incubated 60 min at 20° C. washed five times in TBT and the amount of bound antibody is quantified by the use of a chromogenic peroxidase substrate.

EXAMPLE 5

Clinical Value of Measurements in an AG1-1 ELISA Preferentially Recognising Isomerised and/or Optically Inverted Forms of the Epitope for Monitoring Patients with RA Serum samples from RA patients as well as age matched controls were measured in the assay described above. Furthermore, synovial fluid was measured in the AG1-1 ELISA as described in Example 2.

Figure 4:
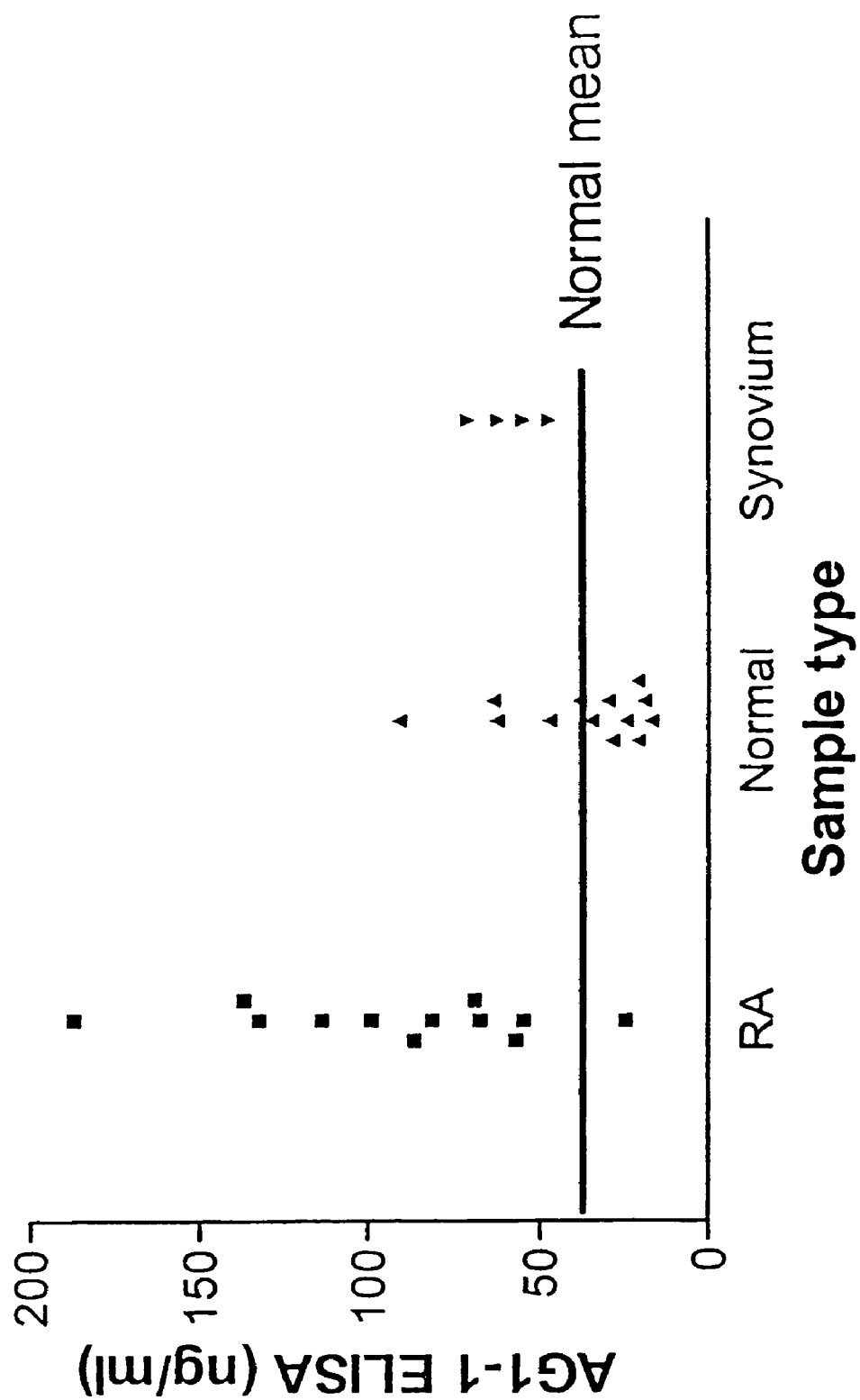
FIG. 4 shows the result of applying the ELISA of FIG. 2 to serum and synovial fluid samples.

Thus FIG. 4 shows the results of the measurement of serum samples from RA patients, and controls in the AG1-1 specific assay. In the right side of the graph, results from measurement of 4 synovial fluid samples are shown. It is remarkable that the assay performs satisfactorily on synovial fluid samples. Normally synovial fluid produces too high a background due to matrix effects from other proteins present for any result to be obtained from an ELISA directed to a cartilage protein fragment.

The data suggest that measurement of isomerised/optically inverted forms of AG1-1 peptide fragments in circulation have a clinical value for diagnosis, monitoring, managing of treatment of RA patients and for clinical evaluation of ongoing cartilage destruction in patients with joint diseases.

EXAMPLE 6

Clinical Value of Measurements in an AG1-1 ELISA Preferentially Recognising Isomerised and/or Optically Inverted Forms of the Epitope for Monitoring Patients with JRA (Juvenile Rheumatoid Arthritis)

Figure 5:
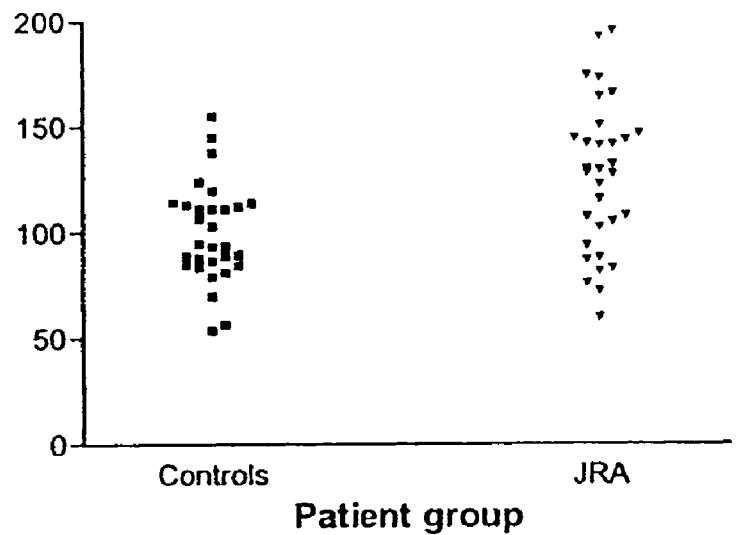
FIG. 5 shows the result of applying the AG1-1 ELISA to patients with juvenile rheumatoid arthritis and controls (Example 6)

An additional clinical evaluation of the AG1-1 serum ELISA described in example 2 has been carried out. This was performed with serum samples from patients with juvenile Rheumatoid Arthritis (JRA) and age matched controls. FIG. 5 shows the results from 30 JRA patients and 32 age matched controls. A non-parametric T-test (Mann-Whitney, two-tailed) shows a highly significant elevation of average AG1-1 concentration (P<0.0001) compared to controls. Also in this experiment a significant elevation among the patient group with joint diseases was seen. Of notice was a complete lack of correlation to SERUM CROSSLAPS measurements (r=0.05; data not shown). SERUM CROSSLAPS One step ELISA is an assay specific for isomerised collagen type I fragments (Rosenquist et al. 1998), and measures in this assay specifically reflects bone resorption. Thus the lack of correlation between the AG1-1 assay and the SERUM CROSSLAPS assay demonstrates that the AG1-1 assay is unaffected by metabolites of collagen type I released during osteoclastic bone resorption. A correlation to the time since diagnosis of JRA was seen (r=−0.44), showing that the AG1-1 concentration is most elevated in the newly diagnosed, untreated patients, where the joint cartilage destruction is occurring at the highest rate.

EXAMPLE 7

Figure 6:
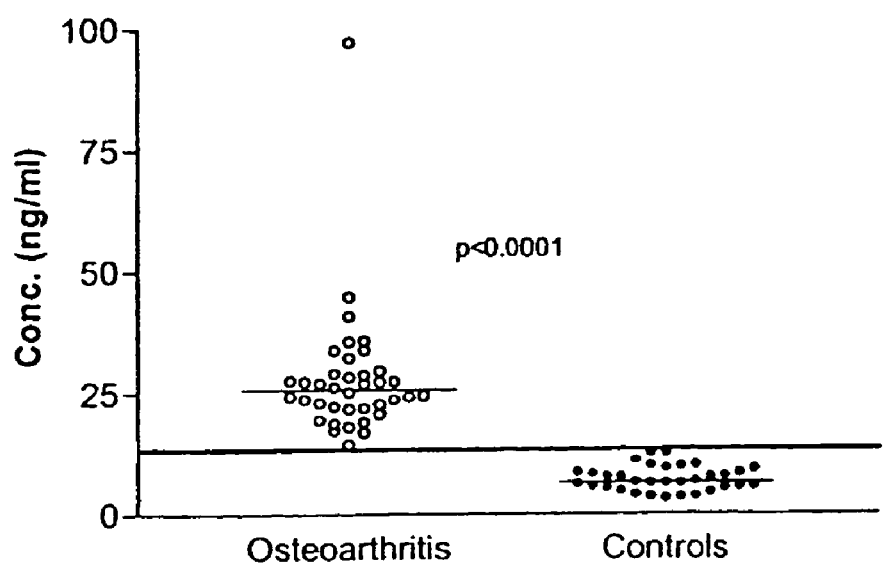
FIG. 6 shows the result of applying the AG1-1 ELISA to osteoarthritis patients and controls (Example 7)

Clinical Value of Measurements in an AG1-1 ELISA Preferentially Recognising Isomerised and/or Optically Inverted Forms of the Epitope for Monitoring Patients with OA In order to provide an assessment of the clinical value of the AG1-1 assay described in example 2 for assessing elevated cartilage metabolism in OA, serum samples from OA patients as well as age matched controls were measured in the assay described above. OA samples from 40 newly diagnosed patients and 40 samples from a matched control group were included in the measurements. FIG. 6 shows the results of measurement of serum samples from OA patients and controls in the AG1-1 specific assay. All OA samples are measured higher than the controls (p<0.0001, Two-tailed Non-parametric T-test, Mann-Whitney).

The data presented in FIG. 6, demonstrate that measurement of isomerised/optically inverted forms of AG1-1 peptide fragments in circulation has a clinical value for diagnosis/monitoring of OA patients and for clinical evaluation of ongoing cartilage destruction in patients with joint diseases.

EXAMPLE 8

Figure 7:
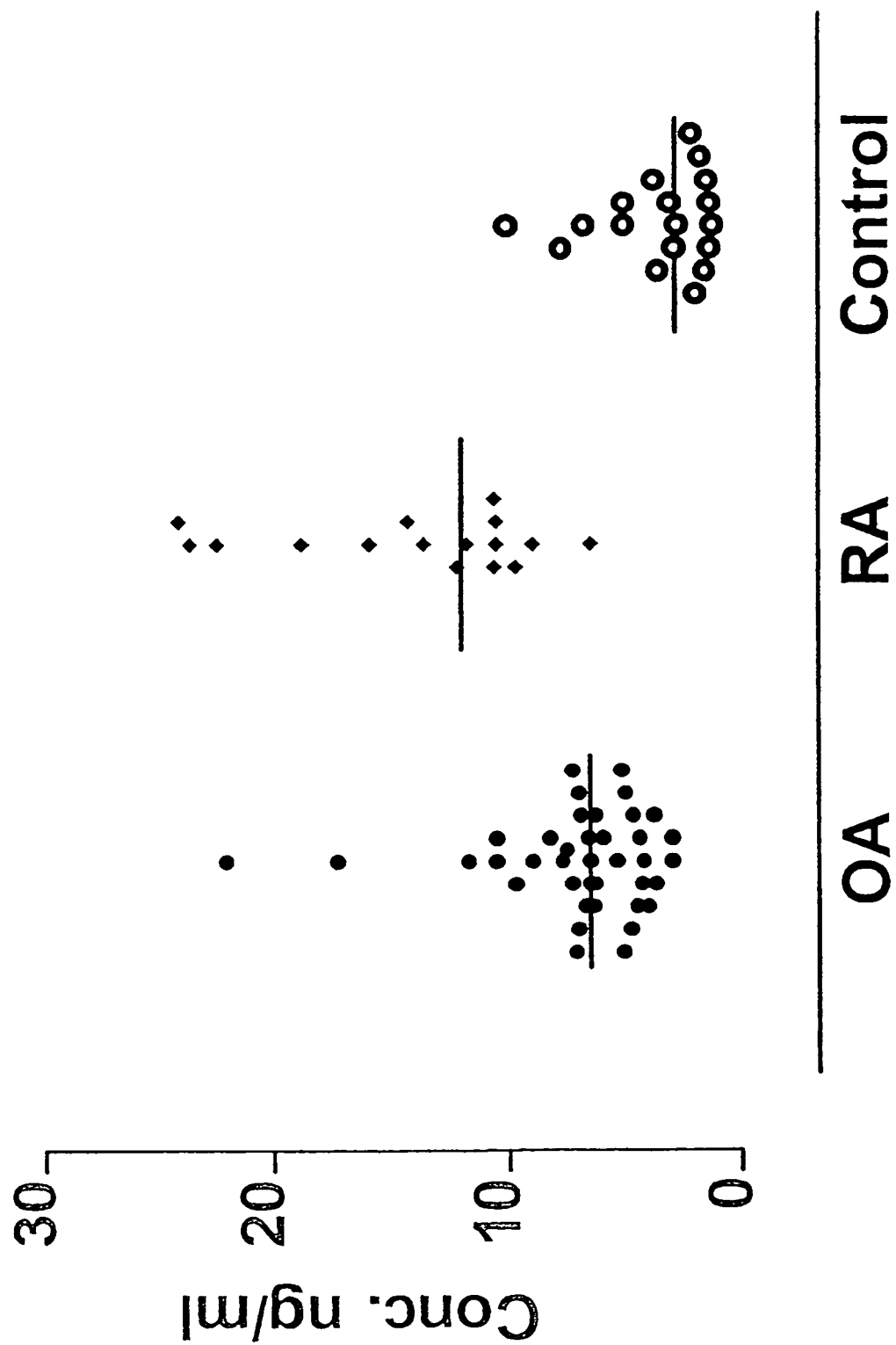
FIG. 7 shows the result of applying the AG1-1 ELISA to osteoarthritis patients and controls (Example 8)

Clinical Value of Measurements in an AG1-1 ELISA Preferentially Recognising Isomerised and/or Optically Inverted Forms of the Epitope for Monitoring Patients with OA and RA Serum samples from patients with OA and matched control samples from healthy individual without arthritis or other diseases affecting joint or cartilage metabolism was measured in the monoclonal AG1-1β assay described in example 3. Samples from 39 newly diagnosed OA patients, from 16 RA patients and 18 samples from a matched control group were included in the measurements. FIG. 7 shows the results of measurement of serum samples from OA patients and controls in the AG1-1β specific assay. The OA and RA samples are measured higher than the controls (p<0.0001, Two-tailed Non-parametric T-test, Mann-Whitney).

The data presented in FIG. 7, demonstrate that measurement of β-Asp isomerised forms of AG1-1 peptide fragments in circulation has a clinical value for diagnosis/monitoring of OA and RA patients and for clinical evaluation of ongoing cartilage destruction in patients with joint diseases.

EXAMPLE 9

Figure 8:
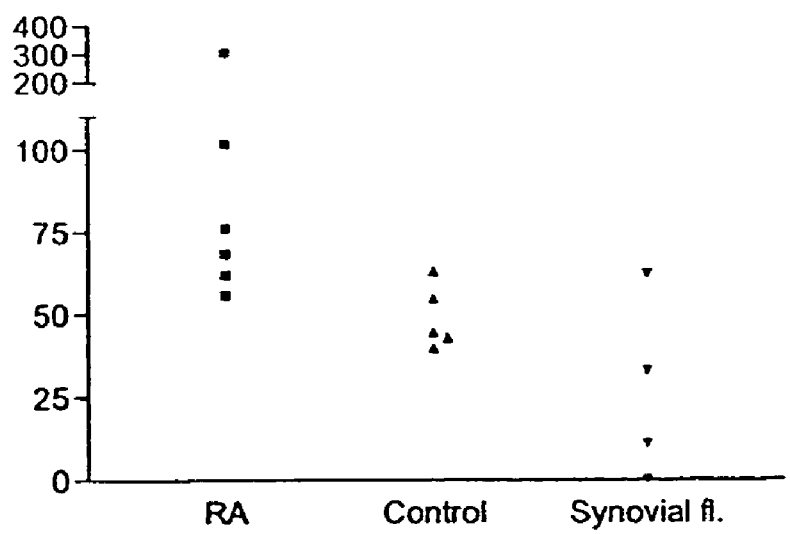
FIG. 8 shows the result of applying the CLP assay of Example 4 to serum from RA patients and controls and synovial fluid samples (Example 9)

Clinical Value of Measurement of Samples from RA Patients in a CLP Specific ELISA, The clinical value of the CLP assay described in example 4 was evaluated by measurement of samples from the RA patients and matched controls. The same sample panels as shown in FIG. 4 with AG1-1 measurements were also measured in the CLP ELISA. FIG. 8 shows the results of measurements on serum samples from patients with RA, controls and synovial fluid samples in the CLP serum ELISA. The average concentration in the RA group was 111.5 ng/ml and in the control group 48.94 ng/ml. The difference was statistically significant as assessed by non-parametric T-test (Mann-Whitney) (p=0.017).

The correlation between measurements in the CLP assay and the AG1-assay was high (r=0.82 excluding one RA sample).

EXAMPLE 10

Figure 9:
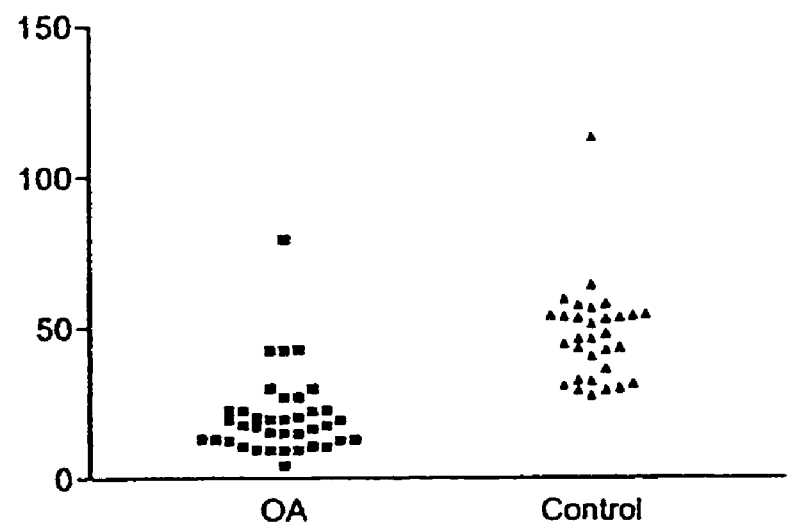
FIG. 9 shows the result of applying the CLP ELISA to serum samples from OA patients and controls (Example 10)

Clinical Value of Measurement of Samples from OA Patients in a CLP Specific ELISA The clinical performance of the CLP assay described in example 4 was further evaluated. The OA sample panel from patients with newly diagnosed active OA depicted in FIG. 6 was also measured in the CLP assay. FIG. 9 shows the differentiation of serum samples from patients with OA and controls in the CLP serum ELISA using antiserum from the rabbit 199025 (the same patient population as measured in the AG1-1 ELISA in FIG. 4). The average concentration in the OA group was 20.6 ng/ml and in the control group 47.3 ng/ml. The difference was statistically significant as assessed by non-parametric T-test (Mann-Whitney) (p<0.0001). The OA patients were measured with a significantly lower CLP concentration than the control group.

EXAMPLE 11

Figure 10:
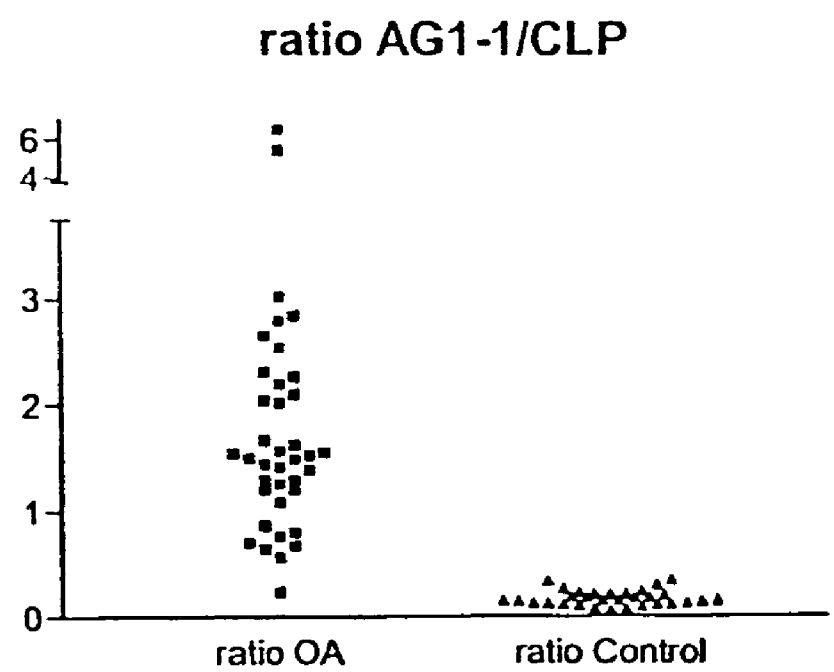
FIG. 10 shows the ratios of AG1-1 ELISA CLP ELISA results for OA patients and controls (Example 11).

Clinical Value of Calculation of a Ratio Between CLP and AG1-1 Measures for Assessment of Joint Diseases The ratio was calculated between the AG1-1 measurements and the CLP measurements of the OA patients and controls (examples 7 and 10). FIG. 10 shows the ratio between AG1-1 and CLP measurements in the OA and control populations shown in FIGS. 4 and 6. The differentiation between the two populations is highly significant, and would allow an establishment of an absolute cut-off value for a 'pathological ratio'. The difference is highly significant with p<0.0001 (two tailed non-parametric T-test). The T-score was 22.4.

From the highly significant differentiation between the two groups, it appears that an absolute cut-off value for the ratio can be determined allowing differentiation between individual patients with normal or abnormal joint metabolism. Such a ratio may be highly relevant for assessment of 'pathological' joint metabolism, it represent a convenient method for normalising the assay for systemic joint metabolism.

Whilst the invention has been described with reference to specific examples, many variations thereof are possible within the scope of the invention.

REFERENCES

1. Møller, H J. Connective tissue markers of Rheumatoid Arthritis. Scand. J. Clin. Lab. Invest. 1998: 58: 269-278.
2. Stucki, G. Langenegger T. Management of rheumatoid arthritis, 1997. Curr Opin. Rheumatol. 9:229-35.
3. Wollheim, F. A. Predictors of joint damage in rheumatoid arthritis. 1996 AMPIS; 104:81-93.
4. Geiger, T. and Clarke, S. (1987). De-amidation, Isomerisation and Racemisation at Asparginyl and Aspartyl Residues in Peptides. J. Biol. Chem. 262(2): 785-794.
5. Clarke, S. (1987). Propensity for Spontaneous Succinimide Formation from Aspartyl and Asparginyl Residues in Cellular Proteins. Int. J. Peptide Protein Res. 30: 808-821.
6. Poole, A. R. Dieppe, P. 1994 Biological markers in rheumatoid arthritis. Sem. Arthr. Rheum. 23: 17-31.
7. Fledelius, C. Johnsen, A. H. Cloos, P. A. C. Bonde, M Qvist, P. 1997. Characterisation of urinary degradation products derived from type I collagen. Identification of a β-isomerised Asp-Gly sequence within the C-telopeptide (α1) region. J. Biol. Chem.; 15:9755-9763.
8. Glant, T. T. Cs-Szabó, G. Nagase, H. Jacobs, J. J. Mikecz, K. 1998. Progressive polyarthritis induced in BalbC mice by aggrecan fragments from normal and osteoarthritic human cartilage. Arthritis Rheum. 41: 1007-1018.
9. Dudhia, J. Davidson, C. M. Wells, T. M. Vynois, D. H. Hardingham, T. E. Bayliss, M. T. 1996. Age related chantes in the content of the C-terminal region of aggrecan in human articular cartilage. Biochem. J. 313: 993-940.
10. Zhang, Y. Guerassimov, A. Leroux, J. Y. Cartman, A. Webber, C. Lalic, R. de Miguel, E. Rosenberg, G. Poole, A. R. 1998. Induction of arthritis in Balb C mice by cartilage link protein: involvement of distinct regins recognised by T and B lymphocytes. Am. J. Pathol. 153: 1283-1291.
11. Radkiewicz, J. L., Zipse, H., Clarke, S., and Houk, K. N. (1996) Accelerated Racemization of Aspartic Acid and Asparagine Residues via Succinimide Intermediates: An ab Initio Theoretical Exploration of Mechanism J. Am. Chem. Soc. 118, 9148-9155.
12. Rafferty B, Coy D H and Poole S (1988) Pharmacokinetic evaluation of superactive analougues of growth hormone-releasing factor (1-29)-amide Peptides 9(1):207-9
13. Van Regenmortel M, and Muller S. (1998) D-peptides as immunogens and diagnostic reagents. Current opinion in Biotechnology, 9:377-382
14. Campbell, A. M., Laboratory Techniques in Biochemistry and Molecular Biology, Vol. 12 (1986).
15. Morein, B. et al., Nature 308:457-460 (1984).
16. Goding, J. W., in Monoclonal Antibodies: Principles and Practice, (1986).
17. E. Ishikawa. Journal of Immunoassay 3:209-327 (1983)).
18. Greg T. Hermanson, "Bioconjugate techniques" 1996, Academic press, San Diego, USA.
19. Neidhart, M. Hauser, N. Paulsson, M. Diceare, P. E. Michel, B. A. and Hauselman, H. J. British Jnl. Of Rhumatology 1997:36: 1151-1160.
20. Lorenzo P, Bayliss, MT, and Heinegard D. (1998a). A Novel Cartilage Protein (CILP) Present in the Mid-zone of Human articular cartilage Increases with age. J. Biol. Chem. 273(36):23463-23468.
21. Lorenzo, P., Neame, P., Sommarin, Y., and Heinegard D. (1998b). Cloning and Deduced Amino Acid Sequence of a Novel Cartilage Protein (CILP) Identifies a Proform Including a Nucleotide Pyrophosphohydrolase. J. Biol. Chem 273(36): 23469-23475.
22. Köhler G, Milstein C. Continuous cultures of fused cells secreting antibody of predefined specificity. Nature 1975; 256: 495-497.
23. Rosenquist C, Fledelius C, Christgau S, Pedersen B J, Bonde M, Christiansen C. The serum CrossLaps One Step ELISA, The first application of monoclonal antibodies for measurement in serum of bone-related degradation products from C-terminal telopeptides of type I collagen. Clin Chem, 1998; 44: 2281-2289.
24. Kearney J F, Radbruch A, Liesegang B, Rajewsky K. A new mouse myeloma cell line that has lost immunoglobulin expression but permits the construction of antibody-secreting hybrid cell lines. J. Immunol. 1979; 123: 1548-1550.
25. Maroudas A, Bayliss M T, Uchitel-Kaushansky N, Schneiderman R, Gilav E. Aggrecan Turnover in Human Articular Cartilage: Use of Aspartic Acid Racemization as a Marker of Molecular Age. Arch Biochemistry and Biophysics 1998; 350: 61-71.

All references disclosed herein are incorporated by reference. Specifically incorporated by reference are the following documents:

U.S. Ser. No. 60/343,384 as filed on Dec. 21, 2001; WO01/38872 as published on 31 May 2001; and GB 9928052.1 as filed in Great Britain on Nov. 26, 1999.

---

The invention claimed is:

1. A method of immunologically measuring the amount of isomerized or optically inverted fragments of aggrecan, comprising immunologically binding in blood, plasma, serum, or synovial fluid isomerised or optically inverted fragments from aggrecan by contacting a sample of blood, plasma, serum, or synovial fluid with an antibody or a binding fragment thereof which specifically binds and preferentially recognizes the amino acid sequence Gly-Arg-Val-Arg-Val-*Asx-Ser-Ala-Tyr (SEQ ID NO:6), wherein *Asx is αD) Asp or αD Asn or is βL Asp or βD Asp, in preference to binding the amino acid sequence Gly-Arg-Val-Arg-Val-Asn-Ser-Ala-Tyr (SEQ ID NO:4); and wherein the antibody or binding fragment thereof discriminates SEQ ID NO:6 from SEQ ID NO:4; and determining the amount of binding thereof to said fragments.

2. A method as claimed in claim 1, wherein said measurement provides an index of cartilage turnover relevant for osteoarthritis or rheumatoid arthritis.

* * * * *